US010092853B2

(12) United States Patent
Ikegami et al.

(10) Patent No.: US 10,092,853 B2
(45) Date of Patent: Oct. 9, 2018

(54) APPARATUS FOR PRODUCING HALOHYDANTOIN COMPOUND

(71) Applicant: NIPPOH CHEMICALS CO., LTD., Tokyo (JP)

(72) Inventors: Tomohiro Ikegami, Isumi (JP); Yukihiko Hanamura, Isumi (JP); Shinji Uchikoshi, Tokyo (JP)

(73) Assignee: NIPPOH CHEMICALS CO., LTD., Tokyo (JP)

( * ) Notice: Subject to any disclaimer, the term of this patent is extended or adjusted under 35 U.S.C. 154(b) by 0 days.

(21) Appl. No.: 15/351,018

(22) Filed: Nov. 14, 2016

(65) Prior Publication Data

US 2017/0056786 A1   Mar. 2, 2017

Related U.S. Application Data

(62) Division of application No. 14/350,097, filed as application No. PCT/JP2013/080918 on Nov. 15, 2013, now Pat. No. 9,855,514.

(30) Foreign Application Priority Data

Dec. 19, 2012 (JP) ................. 2012-277128

(51) Int. Cl.
| | | |
|---|---|---|
| *B01D 3/06* | (2006.01) | |
| *C07D 233/82* | (2006.01) | |
| *C07D 233/74* | (2006.01) | |
| *B01D 3/00* | (2006.01) | |

(52) U.S. Cl.
CPC ............... *B01D 3/06* (2013.01); *B01D 3/007* (2013.01); *C07D 233/74* (2013.01); *C07D 233/82* (2013.01)

(58) Field of Classification Search
CPC ........ B01D 3/06; B01D 3/007; C07D 233/74; C07D 233/82
See application file for complete search history.

(56) References Cited

U.S. PATENT DOCUMENTS

| | | | | |
|---|---|---|---|---|
| 2,385,483 | A | * | 9/1945 | Wolff ..................... B01D 61/18 210/600 |
| 2,392,505 | A | | 1/1946 | Rogers |
| 2,795,556 | A | | 6/1957 | Quinn |
| 4,012,565 | A | | 3/1977 | Freedman |
| 4,100,348 | A | | 7/1978 | Habermeier |
| 4,204,915 | A | | 5/1980 | Kurata et al. |
| 4,745,189 | A | | 5/1988 | Lee et al. |
| 5,780,641 | A | | 7/1998 | Yerushalmi et al. |
| 5,953,456 | A | | 9/1999 | Ikeda et al. |
| 7,897,785 | B2 | | 3/2011 | Inoue |
| 2009/0259050 | A1 | | 10/2009 | Inoue et al. |
| 2011/0087031 | A1 | | 4/2011 | Inoue et al. |
| 2011/0092714 | A1 | | 4/2011 | Inoue et al. |
| 2011/0144350 | A1 | | 6/2011 | Inoue et al. |

FOREIGN PATENT DOCUMENTS

| | | | |
|---|---|---|---|
| CN | 1788564 | A | 6/2006 |
| CN | 102628644 | A | 8/2012 |
| EP | 0001394 | A2 * | 4/1979 ............. B01J 19/14 |
| EP | 0785192 | | 7/1997 |
| EP | 1939184 | | 7/2008 |
| EP | 2937338 | | 10/2015 |
| JP | 34-10025 | | 11/1959 |
| JP | 53-116314 | | 10/1978 |
| JP | 8-325192 | | 12/1996 |
| JP | 09-316057 | | 12/1997 |
| JP | 10-28529 | | 2/1998 |
| JP | 2002-030072 | | 1/2002 |
| JP | 2002-275008 | | 9/2002 |
| JP | 2005-291598 | | 10/2005 |
| WO | 2002/08227 | | 1/2002 |
| WO | 2007/026766 | | 3/2007 |

OTHER PUBLICATIONS

Shaoyun, Zhang, Inorganic chemistry, published May 31, 2008, p. 42.
Office Action for CN Patent Application No. 201380062897.4, dated Aug. 10, 2017, 13 total pages.
Hirata, Mitsuho, Distillation, Kagaku to Seibutsu, vol. 2 (1964), No. 6, pp. 31-36.
Office Action for JP Patent Application No. 2014-553023, dated Aug. 22, 2017, 18 total pages.
Summons to attend oral proceedings for EP Patent Application No. 15154215.6, dated Mar. 28, 2017.
CN Office Action, CN Patent Application No. 201380062930.3 dated Mar. 23, 2016, English translation provided.
European Search Report, EP Patent Application No. 13864539.5 dated Apr. 1, 2016.
International Preliminary Report on Patentability in corresponding PCT/JP2006/317113, dated Sep. 9, 2008.
Decision of the technical board of appeal for EP patent application No. 93106005.7, dated Feb. 12, 1998.
Presentation of Publications and the Like and its notification for 2007-533295, dated Jul. 9, 2010.
Office Action for CN application No. 200680031821.5, dated Feb. 5, 2010.
Office Action for CN application No. 200680031821.5, dated Feb. 24, 2011.
European Search Report for 06797085.5, dated Jun. 18, 2010.
Office Action for EP patent application No. 06797085.5, dated Feb. 3, 2012.
Office Action for EP patent application No. 06797085.5, dated Sep. 11, 2012.

(Continued)

*Primary Examiner* — Amanda L Aguirre
(74) *Attorney, Agent, or Firm* — Casimir Jones, SC; Robert A. Goetz

(57) ABSTRACT

A method of the present invention for producing a halohydantoin compound by refining, in a dryer (1), a composition containing at least one of water and elemental halogen, an organic solvent, and the halohydantoin compound, the method includes the steps of: (i) removing the organic solvent from the composition; and (ii) removing the at least one of the water and the elemental halogen from the composition refined in the step (i).

4 Claims, 1 Drawing Sheet

(56) References Cited

OTHER PUBLICATIONS

European Search Report for EP patent application No. 12180060.1, dated Sep. 28, 2012.
Office Action for EP patent application No. 12180060.1, dated Jun. 12, 2013.
European Search Report for EP patent application No. 12180061.9, dated Oct. 2, 2012.
Office Action for EP patent application No. 12180061.9, dated Sep. 18, 2013.
Summons to attend oral proceedings for EP patent application No. 12180061.9, dated Apr. 11, 2014.
European Search Report for EP patent application No. 15154215.6, dated Jun. 12, 2015.
Office Action for EP patent application No. 15154215.6, dated Aug. 1, 2016.
Office Action for IN patent application No. 858/KOLNP/2008, dated May 9, 2013.
Office Action for IN patent application No. 858/KOLNP/2008, dated May 14, 2015.
Office Action for JP patent application No. 2007-533295, dated Jun. 19, 2012.
Office Action for JP patent application No. 2012-180595, dated Feb. 18, 2014.
Office Action for JP patent application No. 2012-180595, dated Oct. 7, 2014.
Office Action for JP patent application No. 2014-266271, dated Dec. 15, 2015.
Office Action for JP patent application No. 2014-266271, dated Aug. 2, 2016.
Office Action for U.S. Appl. No. 11/991,285, dated Aug. 26, 2009.
Office Action for U.S. Appl. No. 11/991,285, dated Dec. 3, 2009.
Office Action for U.S. Appl. No. 11/991,285, dated Jun. 7, 2010.
Office Action for U.S. Appl. No. 12/926,900, dated Feb. 15, 2013.
Office Action for U.S. Appl. No. 12/926,900, dated Dec. 5, 2013.
Office Action for U.S. Appl. No. 12/926,899, dated Jan. 31, 2012.
Office Action for U.S. Appl. No. 12/926,899, dated Sep. 14, 2012.
Office Action for U.S. Appl. No. 12/926,899, dated Jan. 30, 2013.
Office Action for U.S. Appl. No. 12/926,899, dated Jun. 20, 2013.
Office Action for U.S. Appl. No. 12/926,898, dated Feb. 14, 2013.
Office Action for U.S. Appl. No. 12/926,898, dated Aug. 23, 2013.
Franks, Felix "Freeze-drying of bioproducts: putting principles into practice" (European Journal of Pharmaceuticals and Biopharmaceuticals, 45, (1998); p. 221-229).
Raab et al., "Carbon-14 Labelling of a Trifluolomethoxy Group: Synthesis of a Substance P Antagonist" J Labelled Cpd Radiopharm, 2001, vol. 44, pp. 815-829.
Harker, J.H. et al., Chapter16: "Drying", Chemical Engineering, Jan. 1, 2002, Elsevier Butterworth-Heinemann, XP002584711, ISBN:0750644451, vol. 2.
Japanese Industrial Standards Committee, JIS Handbook 49, Version 2004, Chemical Analysis, front page English language translation only, pp. 1-20.
Kouniaki et al. The effect of high hydrostatic pressure on anthocyanins and ascorbic acid in blackcurrants (Ribes nigrum) (Flavour. Fragr. J. 2004; 19: 281-286).
Aquabrome's Safety Data Sheet by Biolab (1-bromo-3-chloro-5,5-dimethylhydantoin—Jul. 2005), six pages.
Questions and Answers on USP 797. (May 5, 2007). Retrieved from http://www.usp797.org/QA-E9.htm—May 5, 2007, three pages.
Stahl et al. "The effect of process variables on the degradation and physical properties of spray dried insulin intended for inhalation" (Int. J. Pharm. (Feb. 21, 2002), 233(1-2); pp. 227-237).
Vapor Pressure. (Oct. 1999). Retrieved from http://hyperphysics.phy-astr.gsu.edu/hbase/kinetic/vappre.html-VaporPressure—Oct. 1999 pp. 1-4.
Office Action, U.S. Appl. No. 14/350,098, dated Jan. 9, 2017.
Mullin, J.M. "Sublimation" Ullmann's Encyclopedia of Industrial Chemistry, 2003, 34, 535-555.
International Search Report, International Patent Application No. PCT/JP2013/080916, dated Dec. 17, 2013.
International Preliminary Report on Patentability, International Patent Application No. PCT/JP2013/080916, dated Jul. 2, 2015.
Office Action for U.S. Appl. No. 14/350,097, dated Mar. 7, 2017.
Restriction Requirement for U.S. Appl. No. 14/350,098, dated Sep. 23, 2016.
Office Action, U.S. Appl. No. 15/351,032, dated May 18, 2017.
Office Action for corresponding Japanese Patent Application No. 2014-553022, dated Aug. 8, 2017.
Orazi et al.,"N-Iodohydantoins, II. Iodinations with 1, 3-Diiodo-5, 5-dimethylhydantoin," J. Org. Chem., 1965, vol. 30, p. 1101-1104.
SIGMA ALDRICH Corp., ALDRICH Chemistry, Handbook of Fine Chemicals, 2009-2010, 2009, p. 867.
International Search Report, International Patent Application No. PCT/JP2013/080918, dated Dec. 17, 2013.
International Preliminary Report on Patentability, International Patent Application No. PCT/JP2013/080918, dated Jul. 2, 2015.
European Search Report, EP Patent Application No. 13864692.2, dated Apr. 6, 2016.
Restriction Requirement, U.S. Appl. No. 14/350,097, dated Sep. 22, 2016.

\* cited by examiner

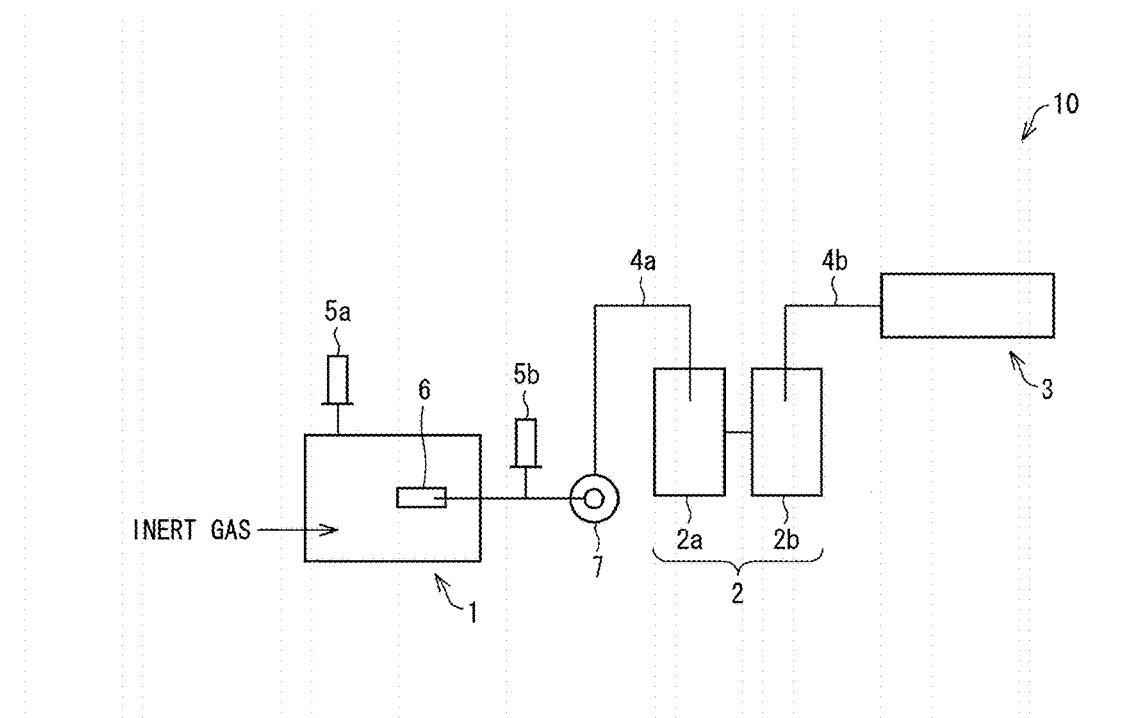

APPARATUS FOR PRODUCING HALOHYDANTOIN COMPOUND

TECHNICAL FIELD

The present invention relates to a method and an apparatus each for producing a halohydantoin compound, a recycling system and a halohydantoin compound.

BACKGROUND ART

Halohydantoin compounds have been widely used as a sensitizer for a photograph or the like or as a halogenating agent or an oxidizing agent for use in a process of producing a medicinal product, an agricultural chemical, a chemical compound, or the like. The halohydantoin compounds are considered as a promising compound because the halohydantoin compounds are stable and can be more economically produced by a known method. One of such halohydantoin compounds is 1,3-diiodo-5,5-dimethylhydantoin. As a method for producing 1,3-diiodo-5,5-dimethylhydantoin, for example, a method including the step of causing 5,5-dimethylhydantoin and iodine monochloride to react with each other in the presence of a base in a mixed solvent of an aqueous solution of a base and an organic solvent and a refining method have been disclosed (see, for example, Patent Literature 1 and Non-Patent Literature 1).

Non-Patent Literature 1 describes the following method: 5,5-dimethylhydantoin and iodine monochloride are reacted with each other with use of a sodium hydroxide aqueous solution and carbon tetrachloride. The resulting crystals are washed with water, and are further washed with anhydrous ethyl acetate. After that, the crystals are dried at 60° C. under a reduced pressure and thereby, 1,3-diiodo-5,5-dimethylhydantoin is refined. Non-Patent Literature 1 further states that the resulting 1,3-diiodo-5,5-dimethylhydantoin is a reagent so stable that it can be preserved without recrystallizing in a desiccator in a dark place.

Further, Patent Literature 1 gives the following description: First, 5,5-dimethylhydantoin and iodine monochloride are reacted with each other in a sodium hydroxide aqueous solution with use of N,N-dimethylformamide or an n-butyl acetate solvent. Next, the precipitated crystals as a result of the reaction are collected by filtration, and then, dried under a reduced pressure, thereby being refined.

CITATION LIST

Patent Literature 1
Japanese Patent Application Publication, Tokukai, No. 2002-30072 A (Publication Date: Jan. 29, 2002)
Non-Patent Literature 1
ORFEO O. ORAZI., et al., N-Iodohydantoins. II. Iodinations with 1,3-Diiodo-5,5-dimethylhydantoin, J. Org. Chem., 1965, Vol. 30, p. 1101-1104

SUMMARY OF INVENTION

Technical Problem

With the refining method described in Non-Patent Literature 1, 1,3-diiodo-5,5-dimethylhydantoin contains 65% of effective iodine, and the yield of 1,3-diiodo-5,5-dimethylhydantoin is as low as 75%. Non-Patent Literature 1 makes no mention of the purity of 1,3-diiodo-5,5-dimethylhydantoin.

Further, Patent Literature 1 makes no mention of the purity of 1,3-diiodo-5,5-dimethylhydantoin that is obtained by the refining method described therein.

The inventors of the present invention diligently studied the methods for refining a halohydantoin compound described in these literatures. As a result, the inventors of the present invention finally found the following problems:

A halohydantoin compound is so unstable at a normal temperature that the halohydantoin compound needs to be refrigerated for preservation. Further, when suspended in water, a halohydantoin compound gradually decomposes to liberate iodine. Furthermore, when heated in the state being a wet material containing a certain or lager amount of a mixed liquid component such as a mixture of water and an organic solvent, a halohydantoin compound problematically becomes more unstable. The halohydantoin compound consequently decomposes to liberate a hydantoin compound and iodine. This undesirably causes a decrease in purity of the halohydantoin compound. Further, the iodine thus liberated undesirably causes coloring of the halohydantoin compound and corrosion of refining equipment.

The present invention has been made in view of the foregoing problems, and it is an object of the present invention to provide a method for producing a halohydantoin compound by removing a component such as an organic solvent from a composition containing the halohydantoin compound while inhibiting the halohydantoin compound from decomposing to invite coloring of the halohydantoin compound and corrosion of the equipment.

Solution to Problem

In order to solve the above problem, the inventors of the present invention made diligent studies and as a result found out that when a halohydantoin compound containing an organic solvent is dried at a high temperature, decomposition of the halohydatoin compound is accelerated. Consequently, the inventors of the present invention have attained the present invention.

In other words, a production method of the present invention is attained in view of the above object and the production method is a method for producing a halohydantoin compound by refining, in a dryer, a composition containing at least one of water and elemental halogen, an organic solvent, and the halohydantoin compound, the method including the steps of: (i) removing the organic solvent from the composition, at a temperature in a range of not less than 15° C. and not greater than 60° C.; and (ii) removing the at least one of the water and the elemental halogen from the composition refined in the step (i).

A production apparatus of the present invention is attained in view of the above object, and the apparatus is an apparatus for producing a halohydantoin compound, the apparatus refining a composition containing at least one of water and elemental halogen, an organic solvent, and the halohydantoin compound, the apparatus including: a dryer for drying the composition so as to remove a component except the halohydantoin compound from the composition; pressure control means for controlling a pressure in the dryer; a collection tank for collecting the component removed from the composition, the collection tank being connected to the dryer via a duct; and heating means for heating the duct.

A recycling system of the present invention is attained in view of the above object and the recycling system is a system having the steps of refining a composition containing at least one of water and elemental halogen, an organic solvent, and a halohydantoin compound and recovering a component removed by refining, the recycling system including the steps of: (a) preparing the composition; (b) after the step (a), removing first the organic solvent from the composition and then at least one of the water and the elemental halogen from the composition; and (c) collecting the component removed in the step (b) and recovering the component collected, for use in the step (a) to be newly carried out.

A halohydantoin compound of the present invention is arranged so as to have a water content of not greater than 3 weight %.

Advantageous Effects of Invention

The present invention advantageously makes it possible to produce a halohydantoin compound by removing a component such as an organic solvent from a composition containing the halohydantoin compound while inhibiting the halohydantoin compound from decomposing to invite coloring of the halohydantoin compound and corrosion of equipment.

BRIEF DESCRIPTION OF DRAWINGS

The FIGURE is a view schematically illustrating an arrangement of one embodiment of a production apparatus according to the present invention.

DESCRIPTION OF EMBODIMENTS

A production method of the present invention is for producing a halohydantoin compound by refining, in a dryer, a composition containing at least one of water and elemental halogen, an organic solvent, and the halohydantoin compound, and includes the first step (i) of removing the organic solvent from the composition, at a temperature in a range of not less than 15° C. and not greater than 60° C. and the second step (ii) of removing the at least one of the water and the elemental halogen from the composition refined in the first step.

As described above, the halohydantoin compound is unstable when the halohydantoin compound is in the form of a wet material containing a liquid component to a certain extent. On this account, a method for drying this wet material has been provided. However, when the wet material is dried by heating under a reduced pressure so that the wet material is refined, the halohydantoin compound becomes more unstable. As a result, the halohydantoin compound is decomposed. Consequently, the hydantoin compound and elemental halogen are liberated. This decreases a purity of the halohydantoin compound. Moreover, the halohydantoin compound is colored by thus liberated elemental halogen.

In order to solve the above problem, the inventors of the present invention have made diligent studies. As a result, the inventors of the present invention found out that when a halohydantoin compound containing an organic solvent and elemental halogen is dried at a high temperature under a reduced pressure, decomposition of the halohydantoin compound is accelerated. The inventors of the present invention have consequently attained the present invention.

(Composition)

In the production method of the present invention, a composition that is a subject of treatment contains (i) at least one of water and elemental halogen, (ii) an organic solvent, and (iii) a halohydantoin compound. The other components except the halohydantoin compound in the composition, that is, the water, the elemental halogen, and the organic solvent each are a substance whose vapor pressure at 25° C. is not less than 35 Pa. In regard to a content of these substances relative to the entire composition, for example, a lower limit value is preferably 2 weight %, more preferably 5 weight %, or even more preferably 8 weight %, while an upper limit value is preferably 50 weight %, more preferably 45 weight %, or even more preferably 40 weight %. It is possible to suitably use, in particular, a composition whose content of a liquid component including water and the organic solvent is not less than 2 weight % and not greater than 50 weight %. By treating, according to the production method of the present invention, such a composition containing the other components in the above range, it is possible to produce a halohydantoin compound by removing a component such as an organic solvent from a composition containing the halohydantoin compound, while inhibiting the halohydantoin compound from decomposing to invite coloring of the halohydantoin compound and corrosion of equipment.

Note that the term "composition" in the present specification indicates a composition containing a liquid component in the above range and may also be called a "wet material". Further, a compound containing less than 5 weight % of the liquid component as a result of treatment according to the production method of the present invention may be simply referred to as a halohydantoin compound.

In the present specification, the halohydantoin compound can be represented by the following chemical formula I. Note that in the following chemical formula I, a combination of $R_1$, $R_2$, $X_1$ and $X_2$ may be any combination as long as the above range is satisfied.

[Chem. 1]

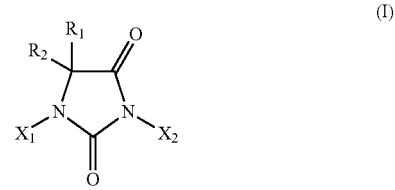

(I)

where:

$R_1$ and $R_2$ are either identical to or different from each other, and are (i) each independently H, a substituted or unsubstituted C1 to C10 aliphatic hydrocarbon group, a substituted or unsubstituted C3 to C10 alicyclic hydrocarbon group, or a substituted or unsubstituted C6 to C10 allyl group or aralkyl group, more preferably H or a C1 to C8 aliphatic hydrocarbon group, or even more preferably H or a methyl group, or (ii) most preferably both methyl groups; and $X_1$ and $X_2$ are either identical to or different from each other, and are (i) each independently H or a halogen atom, more preferably H, Br, or I, or even more preferably H or I, or (ii) most preferably both I, excluding a halohydantoin compound wherein $X_1$ and $X_2$ are both H.

More specifically, preferable examples of the halohydantoin compound encompass 1-bromohydantoin, 1-iodohydantoin, 3-bromohydantoin, 3-iodohydantoin, 1,3-dibromohydantoin, 1,3-diiodo hydantoin, 1-bromo-5-methylhydantoin, 1-iodo-5-methylhydantoin, 3-bromo-5-methylhydantoin, 3-iodo-5-methylhydantoin, 1,3-dibromo-5-methylhydantoin, 1,3-diiodo-5-methylhydantoin, 1-bromo-5,5-dimethylhydantoin, 1-iodo-5,5-dimethylhydantoin, 3-bromo-5,5-dimethylhydantoin, 3-iodo-5,5-dimethylhydantoin, 1,3-dibromo-5,5-dimethylhydantoin, and 1,3-diiodo-5,5-dimethylhydantoin.

Note that all halohydantoin compounds contained in the composition may be identical in composition or alternatively, the above-described plurality of types of composition of the halohydantoin compound may be mixedly present in the composition.

A method for obtaining the halohydantoin compound is not particularly limited, but the halohydantoin compound may be synthesized according to a conventionally known method. One example of a method for synthesizing the halohydantoin compound includes the step of reacting a hydantoin compound and elemental halogen in the presence of a base in an aqueous solution. For example, by reacting a hydantoin compound and an alkali metal salt (NaOH or KOH) with each other, a hydantoin metal salt is prepared. Then, this hydantoin metal salt is reacted with iodine monochloride (ICl) or iodine monobromide (IBr). This gives a wet material including a halohydantoin compound, that is, a composition to be treated in the present invention.

As the elemental halogen, for example, at least one kind from among iodine, bromine and chlorine can be employed. As the organic solvent, for example, at least one kind of the following organic solvents can be employed: an ester solvent, an aromatic solvent, an ether solvent and a chlorine solvent each having a boiling point in a range of not less than 30° C. and not greater than 200° C.

Note that examples of the ester solvent encompass methyl acetate, ethyl acetate, propyl acetate, isopropyl acetate, butyl acetate, isobutyl acetate, sec-butyl acetate, tert-butyl acetate, pentyl acetate, hexyl acetate, methyl propionate, ethyl propionate, propyl propionate, butyl propionate, methyl butyrate, ethyl butyrate, propyl butyrate, and butyl butyrate.

Examples of the aromatic solvent encompass benzene, toluene, ethyl benzene, propyl benzene, cumene, butyl benzene, isobutyl benzene, sec-butyl benzene, tert-butyl benzene, o-xylene, m-xylene, p-xylene, mesitylene, 1,2,3-trimethyl benzene, 1,2,4-trimethyl benzene, o-cymene, m-cymene, and p-cymene.

Examples of the ether solvent encompass diethyl ether, dipropyl ether, isopropyl ether, methyl-tert-butyl ether, methyl cyclopentyl ether, dibutyl ether, anisole, ethyl phenyl ether, tetrahydrofuran, tetrahydropyran, and 1,4-dioxane.

Examples of the chlorine solvent encompass chloropropane, chlorobutane, chloropentane, chlorohexane, chloroheptane, chlorooctane, dichloromethane, 1,2-dichloroethane, 1,2-dichloropropane, 1,3-dichloropropane, 2,2-dichloropropane, 1,2-dichlorobutane, 1,3-dichlorobutane, 1,4-dichlorobutane, chloroform, 1,1,1-trichloroethane, 1,1,2-trichloroethane, 1,1,1,2-tetrachloroethane, 1,1,2,2-tetrachloroethane, 1,2,3-trichloropropane, and carbon tetrachloride.

The following discusses one embodiment of the production method of the present invention, by using a production apparatus 10 shown in the FIGURE. The FIGURE is a view schematically illustrating one embodiment of a production apparatus of the present invention.

(Arrangement of Production Apparatus 10)

First, the following discusses an arrangement of the production apparatus 10. The production apparatus 10 is arranged to include a dryer 1, a collection tank 2 and a pressure reducing pump (pressure control means) 3.

The dryer 1 is for drying a composition (hereinafter, referred to as a "wet material") containing at least one of water and elemental halogen, an organic solvent, and a halohydantoin compound. For example, the purity of the halohydantoin compound can be increased by first reducing the pressure in the dryer 1, and then drying the wet material by heating while rotating the dryer 1 and thereby removing a component except the halohydantoin compound. The dryer 1 includes a container in which the wet material is contained, and is arranged so that the interior of the container can be heated with hot water running around the container. Further, a pressure in the dryer 1 is controlled by the pressure reducing pump 3 described below. Note that a method for controlling a temperature and the pressure in the dryer 1 is not limited to the above method.

Various dryers can be used as the dryer 1. For example, as the dryer 1, a rotary container vacuum dryer (conical vacuum dryer, conical dryer), a rotary drum vacuum dryer (drum vacuum dryer), a vacuum belt dryer, a tray vacuum dryer or a tray reduced-pressure dryer, etc. are suitably used. In particular, the rotary container vacuum dryer (conical vacuum dryer) or the rotary drum vacuum dryer (drum vacuum dryer) are preferable for the following reasons: (i) the rotary container vacuum dryer (conical vacuum dryer) or the rotary drum vacuum dryer (drum vacuum dryer) can stir contents of the dryer 1, so that drying efficiency can be improved and agglomeration and lack of uniformity in drying can be prevented; and (ii) the rotary container vacuum dryer (conical vacuum dryer) or the rotary drum vacuum dryer (drum vacuum dryer) is a compact device.

The dryer 1 is connected with the collection tank 2 via a duct 4a so that a gaseous component removed in the dryer 1 can be sent into the collection tank 2. Moreover, between the dryer 1 and an end of the duct 4a which end is connected to the dryer 1 (that is, a section connecting the dryer 1 and the duct 4a), a filter (filtering means, usually made of fluororesin) 6 is provided so that gas (vaporized component) to be sent to the collection tank 2 is filtered. The presence of this filter 6 prevents (i) a solid substance scattered in the dryer 1 from causing blockage in a reduced pressure lines (ducts 4a and 4b) during drying and (ii) pollution or corrosion of the collection tank 2 or the pressure reducing pump 3, thereby consequently improving a collection rate of a target object.

Note that the dryer 1 may be additionally provided with, for example, an inlet for introducing an inert gas into the dryer 1. This makes it possible to reduce the pressure in the dryer 1 to a pressure lower than the atmospheric pressure while introducing the inert gas into the dryer 1. The inert gas may be any gas as long as the inert gas is inert with respect to the halohydantoin compound. Examples of the inert gas encompass the air, nitrogen, helium, argon, carbon dioxide, etc.

The duct 4a is housed in a tubular pipe (heating means, not shown) and heated by flow of the warm air through the pipe. This makes it possible to prevent a lump of iodine from blocking in the duct 4a. Note that means for heating the duct 4a is not limited to the above arrangement. Further, for the duct 4a, the production apparatus 10 is provided with manometers 5a and 5b for monitoring difference between the pressure in the dryer 1 and the pressure in the duct 4a, and a sight glass 7 for checking blockage in the duct 4a.

The collection tank 2 is a tank for collecting the component removed from the wet material. The collection tank 2 is connected with the duct 4a so that gas discharged from the dryer 1 is sent into the collection tank 2. One collection tank or a plurality of collection tanks may be provided as the collection tank(s) 2. In the present embodiment, two collection tanks (2a and 2b) are provided in series with each other. Specifically, the collection tank 2a is arranged so that the interior of the collection tank 2a is empty and iodine contained in the gas sent in is collected in the collection tank 2a. Meanwhile, liquid for absorbing gas is contained in the collection tank 2b so that elemental halogen (i.e., bromine or chlorine) except iodine, water, an organic solvent, and iodine that has not been collected in the collection tank 2a are collected in the collection tank 2b. As the liquid contained in the collection tank 2b, for example, a reducing-agent containing aqueous solution or an organic solvent can be employed.

Note that although the interior of the collection tank 2a is empty and liquid is contained in the collection tank 2b in the present embodiment, liquid may be contained in the collection tank 2a. In this case, the production apparatus 10 may be arranged to have only one collection tank, and elemental halogen except iodine, water, and an organic solvent are collected in the collection tank 2a. Further, the collection tank 2b may contain liquid, and the liquid may be circulated through the collection tank 2b by once taking the liquid out from the collection tank 2b and pouring the liquid like a shower back into the collection tank 2b. Alternatively, the collection tank 2a may contain liquid, and the liquid may be circulated through the collection tank 2a by once taking the liquid out from the collection tank 2a and pouring the liquid like a shower back into the collection tank 2a. As a further alternative, both the collection tanks 2a and 2b may contain liquid, and the liquid may be circulated through the collection tanks 2a and 2b by once taking the liquid out from the collection tanks 2a and 2b and pouring the liquid like a shower back into the collection tanks 2a and 2b.

The pressure reducing pump 3 is a pump for controlling the pressure in the dryer 1. The pressure reducing pump 3 is connected to the collection tank 2 via the duct 4b, so that the pressure reducing pump 3 reduces the pressure in the dryer 1 via the collection tank 2 and the ducts 4a and 4b. Note that the reduced pressure in the dryer 1 is returned to an ordinary pressure, for example, with nitrogen.

Note that the production apparatus of the present embodiment may be arranged to include, for example, a control system. In this case, various types of processing in the production apparatus can be automated by use of the control system.

Next, the following discusses one embodiment of the production method of the present invention, by using, as an example, a case where the production method of the present invention is carried out in the production apparatus 10.

(First Step)

The first step of the production method of the present invention is the step of removing the organic solvent from the wet material in the dryer 1. In this first step, the wet material is put in the dryer 1. Then, the pressure in the dryer 1 is reduced to a pressure lower than the atmospheric pressure by the pressure reducing pump 3. Then, while the dryer 1 is being rotated, the temperature in the dryer 1 is increased by heating and thereby, the organic solvent is vaporized and removed from the wet material. Note that in the present example, the wet material is dried by employing a conical vacuum dryer while the conical vacuum dryer is being rotated. However, the method for drying the wet material is not limited to this arrangement.

In the first step, at least one of the temperature and the pressure in the dryer 1 may be set lower than that in the second step described below. For example, the lower limit value of the temperature in the dryer 1 in the first step is preferably 15° C., more preferably 25° C., or even more preferably 35° C., while the upper limit value of the temperature in the dryer 1 in the first step is preferably 60° C., more preferably 55° C., or even more preferably 50° C.

Meanwhile, for example, the lower limit value of the pressure in the dryer 1 in the first step is preferably 0.1 kPa, more preferably 0.3 kPa, or even more preferably 0.5 kPa, while the upper limit value of the pressure in the dryer 1 in the first step is preferably 20 kPa, more preferably 15 kPa, or even more preferably 10 kPa.

The organic solvent removed from the dryer 1 is sent into the collection tank 2a and 2b via the duct 4a. As described above, in the present example, the interior of the collection tank 2a is empty while the collection tank 2b contains liquid. Therefore, the organic solvent sent through the duct 4a is collected in the collection tank 2b.

In this way, in the first step, at least one of the temperature and the pressure is set lower than that in the second step. This makes it possible to remove, from the wet material, mainly the organic solvent and elemental halogen. As described above, when the halohydantoin compound containing the organic solvent and elemental halogen is dried at a high temperature under a reduced pressure, decomposition of the halohydantoin compound is accelerated. This decreases the purity of the halohydantoin compound and/or causes coloring of the halohydantoin compound or corrosion of equipment due to the liberated elemental halogen (mainly, iodine). According to the present invention, first, the organic solvent and elemental halogen are removed at a lower temperature under a lower pressure. This makes it possible to prevent decomposition of the halohydantoin compound from accelerating.

Note that, for example, whether or not a content of the organic solvent or elemental halogen contained in the wet material becomes not more than a predetermined value can be used as a criterion for determining when to end the first step. Such a criterion can be set as appropriate according to properties and states of what to be prepared. For example, whether or not the content of the organic solvent in the composition (hereinafter, "crude dried product") refined in the first step becomes preferably not greater than 0.5 weight %, or more preferably not greater than 0.2 weight % can be used as a criterion for determining when to end the first step. In a case where the content of the organic solvent in the composition refined in the first step is not greater than 0.5 weight %, decomposition of the halohydantoin compound can also be prevented at the temperature set in the second step. Alternatively, for example, whether or not the content of elemental halogen in the crude dried product becomes preferably not greater than 0.75 weight % or more preferably, not greater than 0.5 weight % can be used as a criterion for determining when to end the first step. When the content of elemental halogen in the composition refined in the first step is not greater than 0.75 weight %, decomposition of the halohydantoin compound can also be prevented at the temperature set in the second step. Further, after the first step has ended, the reduced pressure in the dryer 1 may be returned to an ordinary pressure and then the pressure is reduced again when the step shifts to the second step.

(Second Step)

The second step in the production method of the present invention is the step of removing at least one of water and elemental halogen from the crude dried product having been refined in the dryer 1. In the second step, the pressure in the dryer 1 containing the crude dried product is reduced by use of the pressure reducing pump 3 and the temperature in the dryer 1 is increased by heating while the dryer 1 is being rotated. At this time, at least one of the temperature and the pressure in the dryer 1 is set higher than that in the first step. This makes it possible to remove at least one of water and elemental halogen from the crude dried product.

For example, the lower limit value of the temperature in the dryer 1 in the second step is preferably 60° C., more preferably 70° C., or even more preferably 75° C., while the upper limit value of the temperature in the dryer 1 in the second step is preferably 100° C., more preferably 95° C., or even more preferably 90° C. Meanwhile, for example, the lower limit value of the pressure in the dryer 1 in the second step is preferably 0.1 kPa, more preferably 0.3 kPa, or even more preferably 0.5 kPa, while the upper limit of the pressure in the dryer 1 in the second step is preferably 25 kPa, more preferably 20 kPa, or even more preferably 15 kPa.

The water and elemental halogen removed from the dryer 1 is sent into the collection tanks 2a and 2b via the duct 4a. In the present example, in the empty collection tank 2a, iodine among elemental halogens is collected. Meanwhile, in the collection tank 2b containing liquid, elemental halogens except iodine and water are collected.

As described above, in the second step, at least one of the temperature and the pressure is set higher than that in the first step. This makes it possible to remove mainly water and elemental halogen from the crude dried product. Because the crude dried product is dried by heating at a sufficiently high temperature under a sufficiently high pressure, the halohydantoin compound can be made into a more stable dried product. Further, when the second step is carried out, the organic solvent has already been removed from the crude dried product. Accordingly, even when the drying by heating is carried out at a high temperature, acceleration of decomposition of the halohydantoin compound is suppressed. This makes it possible to produce a highly-pure halohydantoin compound that is less colored.

Even in a case where the method of the present invention is employed, part of the halohydantoin compound may be decomposed during drying and consequently, elemental halogen may be produced. However, according to the present invention, thus produced elemental halogen can also be suitably removed during drying. Accordingly, even in the case of a composition containing elemental halogen initially (i.e. in the wet material), the elemental halogen can be suitably removed by the method of the present invention and a highly-pure halohydantoin compound can be obtained by refinement.

Note that, for example, whether or not a content of water contained in the crude dried product becomes not more than a predetermined value can be used as a criterion for determining when to end the second step. Such a criterion can be set as appropriate according to properties and states of what to be prepared. For example, whether or not the content of water in the dried product in the second step becomes preferably not greater than 3.0 weight %, more preferably not greater than 2.0 weight %, or most preferably 1.0 weight % can be used as a criterion for determining when to end the second step.

According to the method of the present invention for producing a halohydantoin compound, it is possible to obtain a halohydantoin compound (i) which is suitably dried so that an organic solvent and elemental halogen are removed, and (ii) which has the water content of not greater than 3 weight %. When the water content is not greater than 3 weight %, the halohydatoin compound can be stored without deterioration in purity for not less than one year by refrigeration storage at the temperature of 5° C.

The method of the present invention for producing a halohydantoin compound may further include an additional step following the end of the second step. The additional step may be, for example, the step of further removing at least one of water and elemental halogen, or an organic solvent from the composition.

(Recycling System)

The present invention also provides a system for recycling the organic solvent and the elemental halogen that are removed from the composition and collected in the above-described production method.

A recycling system of the present invention is a system having the steps of refining a composition containing at least one of water and elemental halogen, an organic solvent, and a halohydantoin compound and recovering a component removed by refining, the recycling system including the steps of: (a) preparing the composition; (b) after the step (a), removing first the organic solvent from the composition and then at least one of the water and the elemental halogen from the composition; and (c) collecting the component removed in the step (b) and recovering the component collected, for use in the step (a) to be newly carried out.

The step (a) is for preparing a composition containing at least one of water and elemental halogen, an organic solvent, and a halohydantoin compound. The composition prepared here may be the wet material in the description of the production method of the present invention. As a method for preparing the composition, it is possible to employ the synthesis method described above.

The step (b) is for removing, after the step (a), first the organic solvent from the composition and then at least one of the water and the elemental halogen. More specifically, it is possible to apply, to this step (b), procedures for the first step and the second step in the production method of the present invention.

The step (c) is for collecting the component removed in the step (b) and recovering the component collected, for use in the step (a) to be newly carried out. As the method for collecting the component removed, it is possible to employ the method discussed in the production method of the present invention. Further, how the component is recovered is not particularly limited. For example, it is possible to provide in advance ducts respectively for taking out the organic solvent and the elemental halogen so that the ducts are connected to the collection tanks 2a and 2b of the production apparatus 10 as illustrated in the FIG., and take out the organic solvent and the elemental halogen through the ducts. This makes it possible to recycle thus recovered component in the step of preparing a composition to be newly carried out.

Note that the step (a) of preparing a composition to be newly carried out here indicates the step (a) of newly preparing a composition after the step (c) of recovering the component, that is, the step of synthesizing a wet material containing a halohydantoin compound. In this step (a) of preparing a composition to be newly carried out, the composition can be synthesized by use of the component recovered in the step (c) of recovering the component.

The following discusses in more detail the embodiment of the present invention, providing Examples. Needless to say, the present invention is not limited to the Examples below, and may take various embodiments in terms of details. Further, the present invention is not limited to the description of the embodiment above, but may be altered in various ways by a skilled person within the scope of the claims. Any embodiment based on a proper combination of technical means disclosed is also encompassed in the technical scope of the present invention.

As described above, according to the production method of the present invention, in the first step (i) of removing the organic solvent from the composition, more preferably, the content of the organic solvent is decreased to a range of not greater than 0.5 weight %.

Further, in the production method of the present invention, in the first step (i) of removing the organic solvent from the composition, more preferably, the elemental halogen is removed so that a content of the elemental halogen is decreased to a range of not greater than 0.75 weight %.

Further, in the production method of the present invention, more preferably, at least one of the temperature and the pressure in the dryer is set lower in the first step (i) than in the second step (ii).

Further, in the production method of the present invention, more preferably, the temperature in the first step (i) is in a range of not less than 15° C. and not greater than 60° C., and the temperature in the second step (ii) is in a range of not less than 60° C. and not greater than 100° C.

Further, in the production method of the present invention, more preferably, in the first step (i), the pressure is in a range of not less than 0.1 kPa and not greater than 20 kPa; and in the second step (ii), the pressure is in a range of not less than 0.1 kPa and not greater than 25 kPa.

Further, in the production method of the present invention, the organic solvent can suitably be at least one selected from among an ester solvent, an aromatic solvent, an ether solvent, and a chlorine solvent each having a boiling point in a range of not less than 30° C. and not greater than 200° C. under an atmospheric pressure.

Further, in the production method of the present invention, the elemental halogen can suitably be at least one selected from among iodine, bromine and chlorine.

Further, according to the production method of the present invention, more preferably, the halohydantoin compound is a compound represented by the chemical formula I above.

Further, more preferably, the production apparatus of the present invention further includes filtering means for filtering the component vaporized, the filtering means being connected to a connecting section between the dryer and the duct.

Further, in the production apparatus of the present invention, more preferably, the collection tank contains liquid for absorbing the component vaporized.

Further, in the production apparatus of the present invention, more preferably, the liquid is either a reducing-agent containing aqueous solution or an organic solvent.

EXAMPLES

Quantitative determination of 1,3-diiodo-5,5-dimethylhydantoin was performed by a titration method with a 0.1 N aqueous solution of silver nitrate, and quantitative determination of butyl acetate was performed by an internal reference method of gas chromatography. Quantitative determination of elemental iodine extracted from a sample with use of chloroform was performed by a silver nitrate titration method. The water content was a value obtained by subtracting the content of elemental iodine from the content of a volatile substance. This content of the volatile substance was obtained by measuring a decrease in mass of a sample in a case where the sample was subjected to 2-hour drying at 105° C. under the atmospheric pressure according to "First Method: Method for Drying by Heating under Atmospheric Pressure" in JIS-K0067-1992 4.1.4(1). This is because, although it is usual to measure a water content by using the Karl Fisher apparatus, the present sample is reactive to a Karl Fisher solution and therefore the water content of the present sample cannot be measured Production Example 1: Synthesis of 1,3-diiodo-5,5-dimethylhydantoin First, a composition containing 1,3-diiodo-5,5-dimethylhydantoin (halohydantoin compound) was produced by the following procedures.

First, water (350.5 kg) was fed into a 1000-L glass lining reaction pot and secondly 12.0% by weight of NaOH aqueous solution (81.7 kg) was fed into the same reaction pot. Then, 5,5-dimethylhydantoin (31.4 kg, 245.0 mol) was fed into the reaction pot. After that, the mixture was cooled to 6° C.

Next, while a temperature of contents of the reaction pot was maintained at 0° C. to 7° C., an aqueous solution (66.2 kg, 198.0 mol) of 12.0% by weight of NaOH and a butyl acetate solution (76.5 kg, 200.0 mol) of 42.3% by weight of iodine monochloride were dropped into the reaction pot over a period of 2 hours. After the end of the dropping, the resulting product was aged at 6° C. for 15 minutes. Next, the reaction product was filtered with use of a centrifugal filter, and a cake as a result of the filtration was washed with 250 kg of water. The wet material (composition) thus obtained containing 1,3-diiodo-5,5-dimethylhydantoin had a weight of 83.3 kg. Thus obtained wet material contained 73.3 kg (88.0% by weight) of 1,3-diiodo-5,5-dimethylhydantoin, 1.3 kg (1.6% by weight) of elemental iodine, 7.3 kg (8.8% by weight) of water, and 0.8 kg (1.0% by weight) of butyl acetate.

Example 1

In Example 1, a halohydatoin compound was produced by drying, according to the following method, a halohydantoin-compound-containing composition obtained by the method of Production Example 1.

First, 83.3 kg of a wet material of 1,3-diiodo-5,5-dimethylhydantoin obtained by the method of Production Example 1 was put in a conical vacuum dryer having an internal capacity of 1000 L and the first step was carried out. The wet material contained 1,3-diiodo-5,5-dimethylhydantoin whose weight was 73.3 kg (88.0 weight %), elemental iodine whose weight was 1.3 kg (1.6 weight %), water whose weight was 7.3 kg (8.8 weight %) and butyl acetate whose weight was 0.8 kg (1.0 weight %).

More specifically, first, reduction of the pressure was started and after the degree of reduced pressure reaches a given level, a conical vacuum dryer was rotated. At the same time, a heat medium was provided through a jacket of the conical vacuum dryer. Then, drying was carried out for 6 hours. During the drying, the temperature in the dryer was in a range of 32.1° C. to 40.5° C. and the pressure in the dryer was in a range of 4.9 kPa to 6.0 kPa. Subsequently, the reduced pressure was returned to an ordinary pressure with nitrogen and part of a first refined product (crude dried product) was taken out from the conical dryer and analyzed. As a result, it was found that the criterion based on the organic solvent for determining the end of the first step was satisfied because the first refined product contained 91.0 weight % of 1,3-diiodo-5,5-dimethylhydantoin, 0.38 weight % of elemental iodine, and 0.1 weight % of butyl acetate.

Subsequently, the second step was carried out. More specifically, reduction of the pressure was started and after the degree of reduced pressure reaches a given level, a conical vacuum dryer was rotated. At the same time, a heat medium was provided through the jacket of the conical vacuum dryer. Then, drying was restarted. One hour after this restart of drying, the temperature in the dryer reached 59.6° C. Thereafter, drying was further carried out for three hours. During this 3-hour drying, the temperature in the dryer was in a range of 59.6° C. to 66.8° C. and the pressure in the dryer was in a range of 4.9 kPa to 6.0 kPa. After cooling water was provided through the jacket of the conical vacuum dryer and the temperature in the dryer was cooled down to 30° C., the reduced pressure was returned to an ordinary pressure with nitrogen and a second refined product (dried product) was taken out from the conical vacuum dryer. The weight of thus obtained second refined product was 71.7 kg. The weight of 1,3-diiodo-5,5-dimethylhydantoin contained in the second refined product was 69.5 kg (97.0 weight %) and the weight of water contained in the second refined product was 1.6 kg (2.3 weight %), but elemental iodine and butyl acetate were not detected. The color of this second refined product was pale yellow. Further, it was found as a result of measurement by dry sieving that 100% of the second refined product had a particle size of less than 8 mm and there was no particle having a particle size of not less than 8 mm.

Examples 2 Through 4

In Examples 2 through 4, by use of a wet material obtained in the same manner as in Production Example 1, refinement was carried out in the same manner as in Example 1. Note that Examples 2 through 4 are different from Example 1 in temperature, pressure, and drying time set for each of the first step and the second step. Table 1 shows respectively set values and respective purities of refined products obtained as a result of thus set values.

TABLE 1

|  | Examples | 2 | 3 | 4 |
|---|---|---|---|---|
| Feed | Amount of Fed Wet material (kg) | 45.5 | 40.0 | 40.0 |
|  | Purity of Wet material (weight %) | 88.2 | 88.1 | 88.8 |
| First Step | Temperature in Dryer (° C.) | 22-41 | 22-39 | 20-42 |
|  | Pressure in Dryer (kPa) | 5.0-6.0 | 5.3-5.7 | 6.2-7.6 |
|  | Drying Time (Hr) | 6 | 4 | 5 |
|  | Purity of First Refined Product (weight %) | 91.6 | 91.8 | 91.1 |
| Second Step | Temperature in Dryer (° C.) | 60-69 | 67-71 | 66-73 |
|  | Pressure in Dryer (kPa) | 4.6-5.5 | 5.2-5.9 | 6.0-8.8 |
|  | Drying Time (Hr) | 6 | 5 | 6 |
|  | Purity of Second Refined Product (weight %) | 95.4 | 97.9 | 96.7 |

As shown in Table 1, in any of Examples 2 through 4, a refined product of 1,3-diiodo-5,5-dimethylhydantoin having a high purity was obtained. Further, all the refined products were slightly colored. In addition, it was found as a result of measurement by dry sieving that 100% of the respective second refined products had a particle size of less than 8 mm and there was no particle having a particle size of not less than 8 mm.

Example 5

In Example 5, a halohydantoin compound was produced by drying a halohydantoin-compound-containing composition synthesized in the above-described Production Example 1. The drying in Example 5 was carried out by the following method.

First, 270.9 kg of a wet material of 1,3-diiodo-5,5-dimethylhydantoin obtained in the same manner as in Production Example 1 was put in a conical vacuum dryer having an internal capacity of 1000 L and the first step was carried out.

More specifically, after the conical vacuum dryer was rotated, reduction of pressure was started. At the same time, a heat medium was provided through a jacket of the conical vacuum dryer. Then, drying was carried out for 6 hours. During the drying, the pressure in the dryer was in a range of 2.7 kPa to 4.3 kPa. Subsequently, the reduced pressure was returned to an ordinary pressure with nitrogen and part of a first refined product (crude dried product) was taken out from the conical vacuum dryer. The weight of thus obtained first refined product was 260.2 kg. Further, the first refined product contained 1,3-diiodo-5,5-dimethylhydantoin whose weight was 236.5 kg (90.9 weight %), water whose weight was 21.0 kg (8.1 weight %), and butyl acetate whose weight was 0.2 kg (0.1 weight %). In a first collection tank, 0.1 kg of elemental iodine was collected, while in a second collection tank, 6.9 kg of water and 3.7 kg of butyl acetate were collected.

Subsequently, the first refined product was put back into the conical vacuum dryer and the second step was carried out. More specifically, the conical vacuum dryer was first rotated and reduction of pressure was started. At the same time, a heat medium was provided through the jacket of the conical vacuum dryer. Then, drying was carried out for 6.5 hours. During the drying, the pressure in the dryer was in a range of 2.1 kPa to 10.5 kPa. After cooling water was provided through the jacket of the conical vacuum dryer and the temperature in the dryer was cooled down to 30° C., the reduced pressure was returned to an ordinary pressure with nitrogen and a second refined product (dried product) was taken out from the conical vacuum dryer. The weight of thus obtained second refined product was 239.2 kg. The second refined product contained 1,3-diiodo-5,5-dimethylhydantoin whose weight was 230.5 kg (96.4 weight %) and water whose weight was 2.0 kg (0.8 weight %). The color of this second refined product was pale yellow. Furthermore, in the first collection tank, 2.0 kg of elemental iodine was collected, while in the second collection tank, 19 kg of water was collected. The elemental iodine collected in the first collection tank was treated with alkaline sulfite aqueous solution and recovered as iodine salts and further recovered as elemental iodine by chlorine oxidation of the iodine salts.

Example 6

In Example 6, a halohydantoin compound was obtained by drying a halohydantoin-compound-containing composition obtained in the same manner as in the Production Example 1. This drying in Example 6 was carried out by the following method.

First, 265.29 kg of a wet material of 1,3-diiodo-5,5-dimethylhydantoin obtained in the same manner as in Production Example 1 was put in a conical vacuum dryer having an internal capacity of 1000 L and the first step was carried out. The wet material contained 1,3-diiodo-5,5-dimethylhydantoin whose weight was 236.8 kg (87.4 weight %), water whose weight was 27.9 kg (10.3 weight %), and butyl acetate whose weight was 3.7 kg (1.4 weight %).

More specifically, the conical vacuum dryer was first rotated, and reduction of pressure was started. At the same time, a heat medium was provided through a jacket of the conical vacuum dryer. Then, drying was carried out for 6 hours. During the drying, the pressure in the dryer was in a range of 3.8 kPa to 7.1 kPa. Subsequently, the reduced pressure was returned to an ordinary pressure with nitrogen and part of a first refined product (crude dried product) was taken out from the conical vacuum dryer and analyzed. As a result, it was found that the first refined product contained 90.9 weight % of 1,3-diiodo-5,5-dimethylhydantoin, 8.1 weight % of water, and 0.1 weight % of butyl acetate. In a first collection tank, 0.1 kg of elemental iodine was collected, while in a second collection tank, 6.9 kg of water and 3.7 kg of butyl acetate were collected.

Subsequently, the second step was carried out. More specifically, the conical vacuum dryer was first rotated and reduction of pressure was started. At the same time, a heat medium was provided through the jacket of the conical vacuum dryer. Then, drying was carried out for 6 hours. During the drying, the pressure in the dryer was in a range of 3.7 kPa to 9.4 kPa. After cooling water was provided through the jacket of the conical vacuum dryer and the temperature in the dryer was cooled down to 30° C., the reduced pressure was returned to an ordinary pressure with nitrogen and a second refined product (dried product) was taken out from the conical vacuum dryer. The weight of thus obtained second refined product was 239.2 kg. The second refined product contained 1,3-diiodo-5,5-dimethylhydantoin whose weight was 230.5 kg (96.1 weight %) and water whose weight was 2.0 kg (0.8 weight %). The color of this second refined product was pale yellow. Furthermore, in a first collection tank, 2.0 kg of elemental iodine was collected, while in a second collection tank, 19 kg of water was collected. The elemental iodine collected in the first collection tank was treated with alkaline sulfite aqueous solution and recovered as iodine salts and further recovered as elemental iodine by chlorine oxidation of the iodine salts.

Example 7

In Example 7, a second refined product was obtained by refining, in the same manner as in Example 1, a halohydantoin-compound-containing composition obtained in the same manner as in Production Example 1. Thus obtained second refined product contained 1,3-diiodo-5,5-dimethylhydantoin whose purity was 96.9 weight %, and 0.4 weight % of water. Further, this second refined product was analyzed by NMR. As a result, it was found that the second refined product contained 1,3-diiodo-5,5-dimethylhydantoin, 1-iodo-5,5-dimethylhydantoin, 3-iodo-5,5-dimethylhydantoin and 5,5-dimethylhydantoin, and a weight ratio of 1,3-diiodo-5,5-dimethylhydantoin 1-iodo-5,5-dimethylhydantoin: 3-iodo-5,5-dimethylhydantoin: 5,5-dimethylhydantoin was 96.9:1.1:2.0:0.0.

Comparative Example 1

In Comparative Example 1, first, 17.6 kg of 1,3-diiodo-5,5-dimethylhydantoin obtained in the same manner as in Production Example 1 was fed into a conical vacuum dryer having an internal capacity of 200 L. This 1,3-diiodo-5,5-dimethylhydantoin had a purity of 88.7%. Then, the conical vacuum dryer was rotated and reduction of pressure was started. At the same time, heated water whose temperature was controlled in a range of 72° C. to 74° C. was provided through a jacket of the conical dryer. Then, drying was carried out for 9 hours. During the drying, the pressure in the dryer was in a range of 7.2 kPa to 8.2 kPa. After the end of the drying, cooling water was provided through the jacket of the conical vacuum dryer and the temperature in the dryer was cooled down to 30° C. Then, the reduced pressure was returned to an ordinary pressure with nitrogen. Thereafter, a dried product of 1,3-diiodo-5,5-dimethylhydantoin was taken out from the conical vacuum dryer. At this time, a solid colored to dark brown was obtained in the vicinity of a manhole inlet zone or on an inner side of a butterfly valve of the conical vacuum dryer. In addition, black elemental iodine was also observed. It is conceivable that this black elemental iodine was produced by decomposition of 1,3-diiodo-5,5-dimethylhydantoin. As a result of analysis of the dark brown solid, the content of 3-diiodo-5,5-dimethylhydantoin was found to be 91.1 weight %. The dried product of 1,3-diiodo-5,5-dimethylhydantoin was measured by dry sieving. As a result, it was found that 80% of the dried product had a particle size of less than 8 mm, 9% of the dried product had a particle size in a range of 8 mm to 15 mm, and 11% of the dried product had a particle size of more than 15 mm.

In Comparative example 1, the wet material was directly dried at a high temperature under a reduced pressure as described above. It is conceivable that this resulted in decomposition of the halohydantoin compound.

Comparative Example 2

In Comparative Example 2, a halohydantoin-compound-containing composition obtained in the same manner as in Production Example 1 was refined in the same manner as in Comparative Example 1 and thereby, a dried product was obtained. Thus obtained dried product ununiformly contained a solid colored to dark brown and black elemental iodine as in Comparative Example 1. In Comparative Example, a purity of 1,3-diiodo-5,5-dimethylhydantoin was 91.0 weight %. Further, this dried product was analyzed by NMR. As a result, it was found that the dried product contained 1,3-diiodo-5,5-dimethylhydantoin, 1-iodo-5,5-dimethylhydantoin, 3-iodo-5,5-dimethylhydantoin, and 5,5-dimethylhydantoin, and a weight ratio of 1,3-diiodo-5,5-dimethylhydantoin 1-iodo-5,5-dimethylhydantoin: 3-iodo-5,5-dimethylhydantoin: 5,5-dimethylhydantoin was 82.3: 4.5:12.4:0.8. Though analysis values obtained respectively by a titration method with a 0.1 N aqueous solution of silver nitrate and NMR were inconsistent in analysis of a low-purity product, it could be clearly confirmed from comparison with Examples that 1,3-diiodo-5,5-dimethylhydantoin was decomposed during drying.

INDUSTRIAL APPLICABILITY

The present invention can be suitably applied to a method for producing a halohydantoin compound to be used as a sensitizer for a photograph or the like, or a halohydantoin compound used as a halogenating agent or an oxidizing agent for use in a production process of medical products, agricultural chemicals, chemical products, etc.

REFERENCE SIGNS LIST

1 dryer
2a, 2b collection tank
3 pressure reducing pump (pressure control means)
4a, 4b duct
5a, 5b manometer
6 filter (filtering means)
7 sight glass

The invention claimed is:
1. An apparatus for producing a halohydantoin compound, the apparatus refining a composition containing at least one of water and elemental halogen, an organic solvent, and the halohydantoin compound, the apparatus comprising:
- a dryer for drying the composition so as to remove a component except the halohydantoin compound from the composition;
- pressure control means for controlling a pressure in the dryer;
- a collection tank for collecting the component removed from the composition, the collection tank being connected to the dryer via a duct; and
- heating means for heating the duct.

2. The apparatus according to claim 1, further comprising filtering means for filtering the component vaporized, the filtering means being connected to a connecting section between the dryer and the duct.

3. The production apparatus according to claim 1, wherein the collection tank contains liquid for absorbing the component vaporized.

4. The production apparatus according to claim 3, wherein the liquid is either a reducing agent-containing aqueous solution or an organic solvent.

* * * * *